United States Patent
McIntyre et al.

(10) Patent No.: US 8,012,096 B2
(45) Date of Patent: Sep. 6, 2011

(54) SURGICAL DEVICE AND METHOD FOR PERFORMING COMBINATION REVASCULARIZATION AND THERAPEUTIC SUBSTANCE DELIVERY TO TISSUE

(75) Inventors: John McIntyre, Rancho Santa Margarita, CA (US); Elbert Tzeng, Irvine, CA (US)

(73) Assignee: Cardiogenesis Corporation, Kennesaw, GA (US)

( * ) Notice: Subject to any disclaimer, the term of this patent is extended or adjusted under 35 U.S.C. 154(b) by 300 days.

(21) Appl. No.: 11/543,505

(22) Filed: Oct. 5, 2006

(65) Prior Publication Data
US 2007/0088218 A1 Apr. 19, 2007

Related U.S. Application Data
(60) Provisional application No. 60/727,325, filed on Oct. 17, 2005.

(51) Int. Cl.
*A61B 8/14* (2006.01)
(52) U.S. Cl. ....................................... 600/471
(58) Field of Classification Search .................. None
See application file for complete search history.

(56) References Cited

U.S. PATENT DOCUMENTS

| | | | | |
|---|---|---|---|---|
| 4,629,453 A * | 12/1986 | Cooper | ............. | 604/192 |
| 5,575,772 A * | 11/1996 | Lennox | ............. | 604/96.01 |
| 5,792,140 A * | 8/1998 | Tu et al. | ............. | 606/41 |
| 5,899,915 A * | 5/1999 | Saadat | ............. | 606/170 |
| 6,102,926 A * | 8/2000 | Tartaglia et al. | ............. | 606/170 |
| 6,224,584 B1 * | 5/2001 | March et al. | ............. | 604/508 |
| 2007/0282254 A1 * | 12/2007 | Chow | ............. | 604/96.01 |

OTHER PUBLICATIONS

Angoulvant, et al.; Neovascularization derived from cell transplantation in ischemic myocardium; Molecular & Cellular Biochemistry; 2004; p. 133-142; 264.
Ghodsizad, et al.; Intraoperative isolation & processing of BM-derived stem cells; Cytotherapy; 2004;vol. 6 No. 5; 523-526.
Gowdak, et al.; Cell therapy plus transmyocardial laser revascularization for refractory angina; Ann.Thoracic Surgery; 2005; p. 712-714.
Klein, et al.; Autologous bone marrow-derived stem cell therapy in combination with TMLR, . . . ; Heart Surgery Forum; 2004; p. 416-419.
Heilmann, et al.; Transmyocardial laser revascularization combined with vascular endothelial growth factor . . . ; European Jrnl. Cardiothoracic Surgery; 2002; p. 74-80.
Lutter, et al.; The combined use of transmyocardial laser revascularization & fibroblastic growth factor . . . ; European Jrnl Cardio-thoracic Surg.; 2002; p. 753-761.
Horvath, et al.; Improvement of myocardial contractility in a porcine model of chronic ischemia . . . ; Jrnl Thoracic & Cardiovascular Surg.; 2004; p. 1071-1077.
Yamamoto, et al; Histologic evidence that basic fibroblast growth factor enhances the angiogenic . . . ; Basic Research in Cardiology; 2000; V.95; No. 1; p. 55-63.

* cited by examiner

*Primary Examiner* — Nicholas D Lucchesi
*Assistant Examiner* — Pritesh Patel
(74) *Attorney, Agent, or Firm* — Sutherland Asbill & Brennan LLP

(57) ABSTRACT

The present invention contemplates a surgical device for both ablating a channel in a patient's tissue and also delivering a therapeutic agent. The device includes an elongated multi-lumen tube, an elongated tissue ablating assembly, and a therapeutic agent delivery assembly. The therapeutic agent is capable of being delivered into the channel and/or to the surrounding tissue. The device may further include a second multi-lumen tube also capable of delivering therapeutic agents. Although suitable for many operations, the device is particularly well suited for transmyocardial revascularization operations. The present invention also contemplates a procedure for using such a surgical device to ablate a channel in a patient's tissue and also deliver a therapeutic agent.

26 Claims, 5 Drawing Sheets

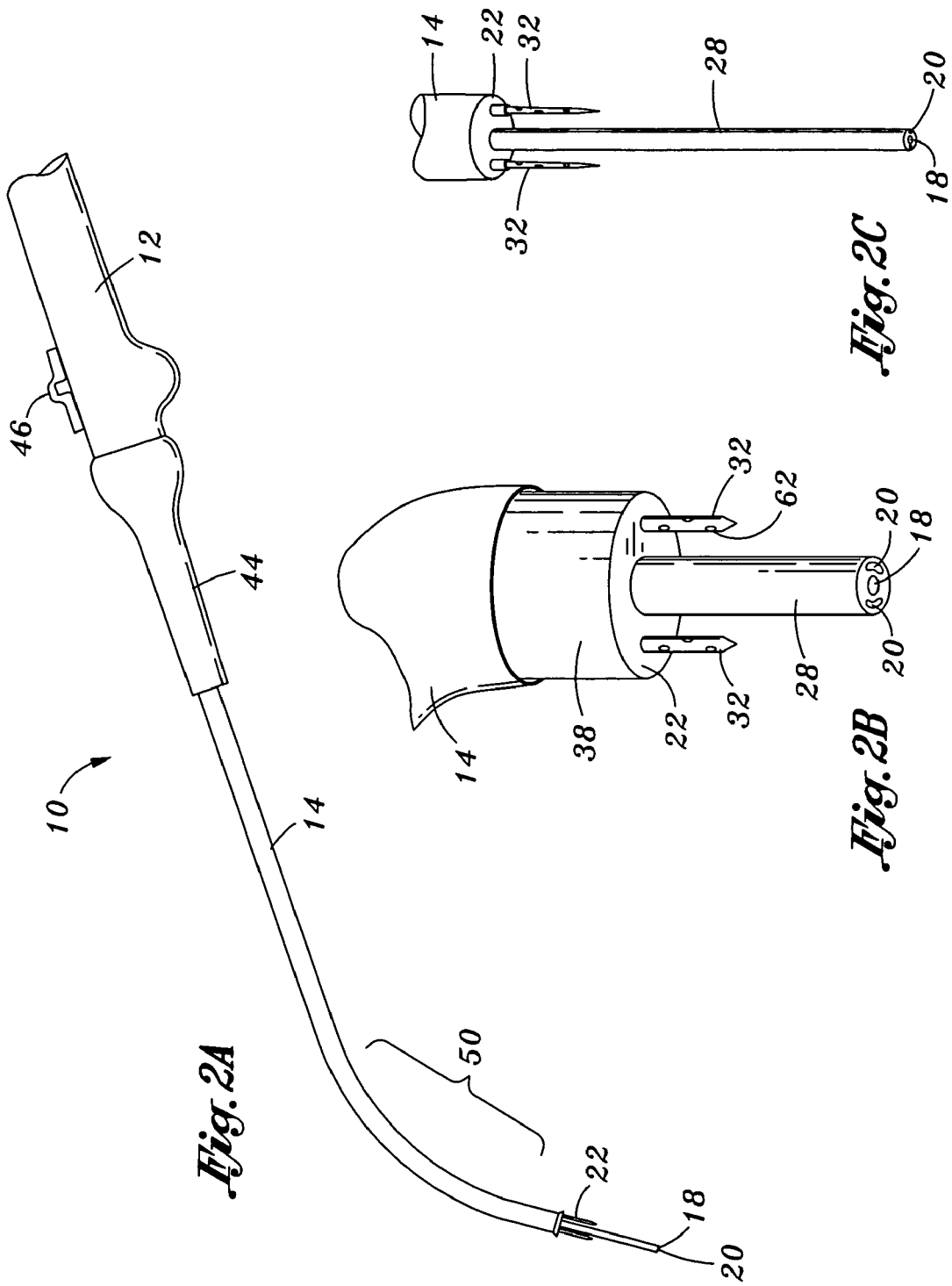

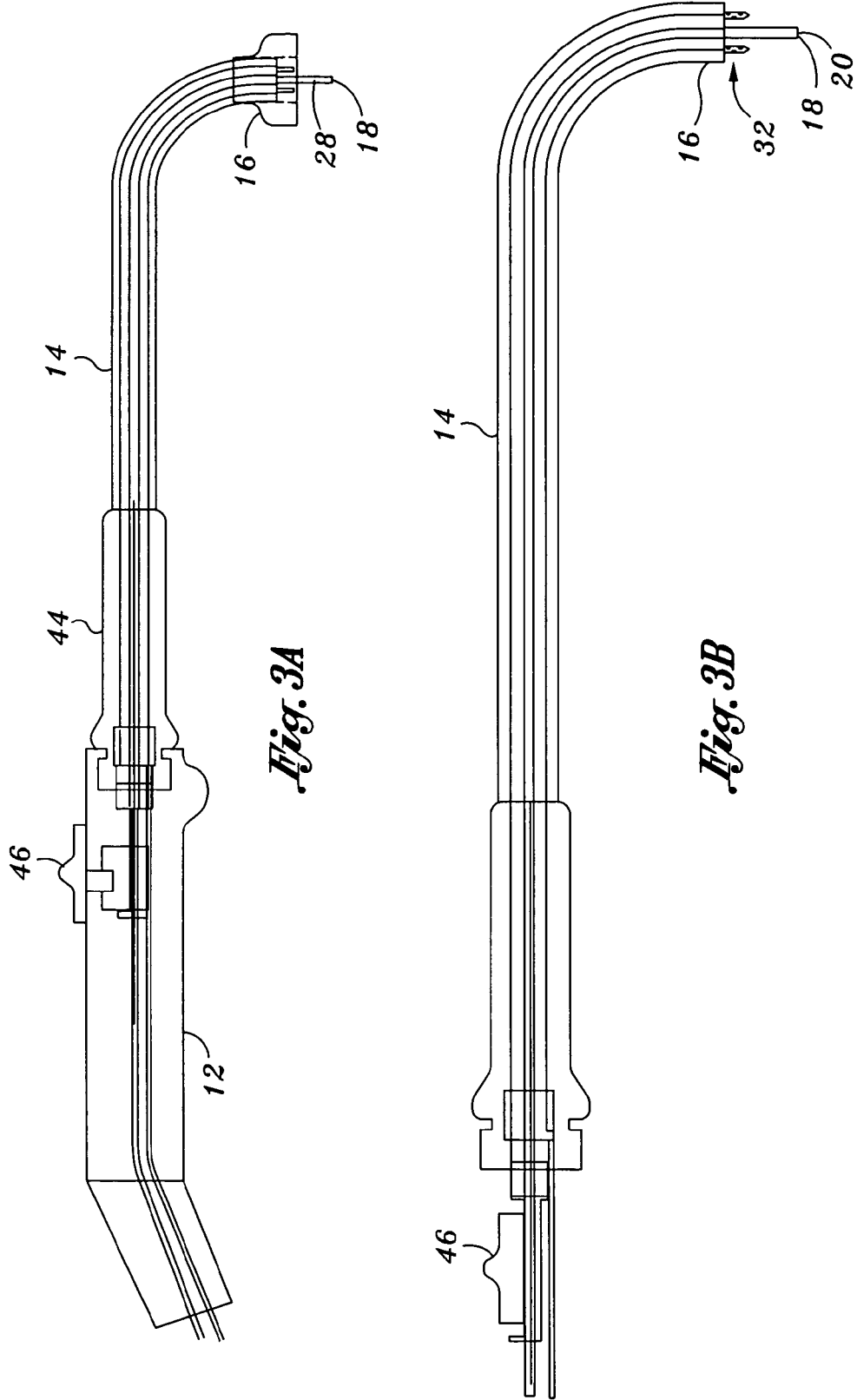

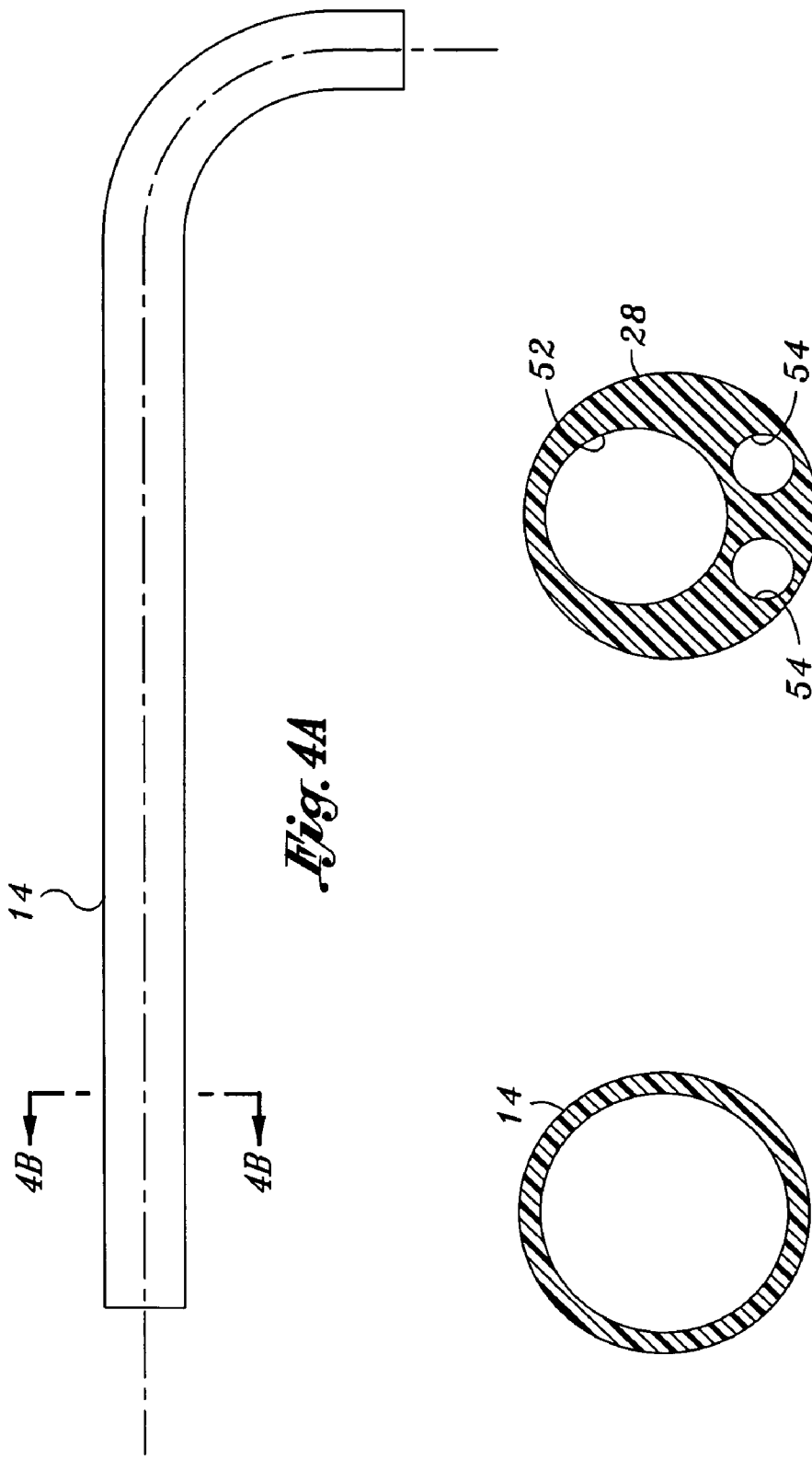

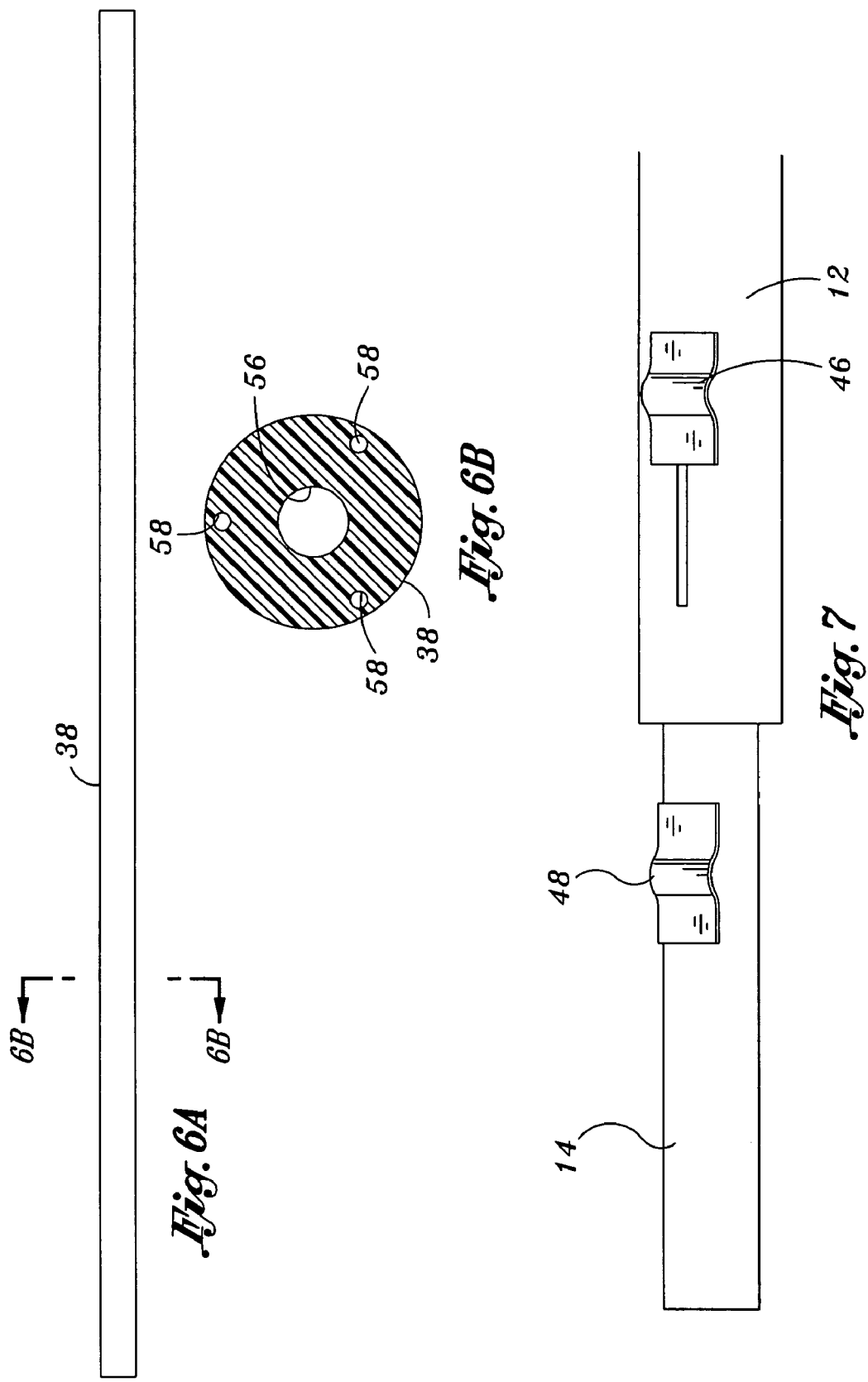

SURGICAL DEVICE AND METHOD FOR PERFORMING COMBINATION REVASCULARIZATION AND THERAPEUTIC SUBSTANCE DELIVERY TO TISSUE

CROSS-REFERENCE TO RELATED APPLICATIONS

This application claims the benefit of U.S. Provisional Application No. 60/727,325, filed on Oct. 17, 2005, the teachings of which are expressly incorporated by reference.

STATEMENT RE: FEDERALLY SPONSORED RESEARCH/DEVELOPMENT

Not Applicable

BACKGROUND

1. Field of the Invention

The present invention relates to a surgical device and method for creating a channel in a region of tissue and simultaneously or promptly thereafter, delivering a therapeutic agent in, near or around the channel and more particularly to a device and method for performing a transmyocardial revascularization procedure in combination with delivery of a therapeutic substance in and around the treated region of the myocardium of the heart.

2. Description of the Prior Art

Living tissue becomes ischemic when starved of oxygen and nutrients, usually because the tissue is not receiving adequate blood supply. Ischemia can be caused by a blockage or narrowing in the vascular system that prohibits an adequate supply of oxygenated blood from reaching the affected tissue area. Ischemia can lead to pain in the area of the affected tissue and, in the case of certain muscle tissue, can interrupt muscular function. Ischemia is reversible, such that cells may return to normal function once they receive the proper blood flow. It is believed ischemic tissue can remain in a hibernating state, preserving its viability for some time despite the deprivation of oxygenated blood. Restoring blood flow to the ischemic region is the only known method to accomplish revival of the ischemic tissue. Although ischemia can occur in various regions of the body, ischemia of the myocardium of the heart is well known due to coronary artery disease or occlusion of the coronary arteries, which otherwise provide blood to the myocardium.

Atherosclerosis or narrowing of the artery is a leading cause for inadequate blood flow to the heart. In addition to the narrowing, atherosclerosis can result in loose plaque dislodging within an artery. This loose plaque can travel through the arterial system until it becomes lodged within a narrower portion of the arterial system. The resulting blockage can lead to an acute infarcted area of the myocardium.

Ischemia and myocardial infarct are two important cardiac disease states. Symptoms are those included in the constellation of symptoms referred to as angina pectoris, and include constricting pain in the chest and radiating pain in the arms, neck and jaw. Ischemia of the tissue of the heart is characterized by limited metabolic processes which causes poor functionality, and may lead to fibrillation and death. Thus, the normal contractile functioning of the myocardial heart cells is hindered in an ischemic region. If an ischemic, or damaged, region of the heart does not receive enough blood flow and nutrients to sustain the myocardial cells, even when in a hibernating state, they are said to die and become infarcted. Infarcted myocardial tissue may also lead to fibrillation and death.

Treatment of myocardial ischemia has been addressed by several techniques designed to restore blood supply to the affected region. One procedure, coronary artery bypass grafting (CABG), involves grafting a venous segment between the aorta and the coronary artery to bypass the occluded portion of the artery. Once blood flow is redirected to the portion of the coronary artery beyond the occlusion, the supply of oxygenated blood is restored to the area of ischemic tissue.

Ischemic myocardium tissue resulting from atherosclerosis can also be treated through stenting the diseased area of the artery. In this procedure, a catheter is passed into the vascular occlusion. A stent is placed at the occlusion site and expanded within the artery to increase the vascular opening and increase blood flow. Alternatively, an angioplasty procedure can be performed to open the narrow vascular passageway. In this procedure, a balloon catheter is passed into the occluded site and the balloon inflated to increase the vascular opening. While effective to increase blood flow for a period of time, these procedures have numerous disadvantages and limitations, including an inability to prevent continued atherosclerosis.

Another method for treating ischemic myocardium is called transmyocardial revascularization ("TMR"), the creation of pathways or channels in the myocardium of the heart. The procedure using needles in a form of surgical "myocardial acupuncture" has been used clinically since the 1960s. In this method, small channels are created either completely through the myocardium in an open surgical procedure or partially through the myocardium from the endocardial layer in a percutaneous procedure. Various modalities may be used to create these channels, including mechanical means, laser energy, radiofrequency energy, ultrasonic energy, resistive heating, and cryoablation. These channels may create an area of injury that is believed to spur the natural healing process. A desirable part of this healing process is the creation of new blood vessels that may help to alleviate the ischemic condition within the myocardium.

Yet another method to treat ischemic tissue, and particularly ischemic myocardial tissue, is through therapeutic agent therapy. Therapeutic agent therapies with angiogenic and myogenic growth factors may expedite and/or augment collateral artery development. In the field of therapeutic agent delivery, many techniques currently exist for delivering therapeutic agents or other materials including, but not limited to, biologics to the human body. These include, among others, oral administration, injection directly into body tissue such as through an intramuscular injection, transcutaneous injection in which a compound is injected directly into the vasculature of a patient, or topical administration. Although many situations are satisfactorily treated by the general or directed, typically systemic acting administration of a therapeutic agent, the treatment of ischemic tissue could be facilitated and/or improved by the ability to deliver or administer a biologic agent directly to or adjacent such tissue with control over such delivery. Recently, medicine has focused attention on treating diseases with conventional physical surgical procedures in combination with a local delivery of a drug or other therapeutic agent. For example U.S. Pat. No. 6,224,584, issued on May 1, 2001 to March, et al., which is hereby incorporated by reference in its entirety into this application, discloses a system for treating a patients heart by first forming channels in the heart and then delivering drugs or other therapeutic agents into those channels.

There are a number of important problems that are not addressed by the systems and methods of the present art. For example, none of the prior art teaches how to ablate a channel into a desired tissue and either simultaneously, or in various sequences, administer a therapeutic agent or any combination of agents into both the channel and into the tissue surrounding the channel. Moreover, the prior art does not teach a device and method for precise and effective ablation along with simultaneous controlled delivery of the desired agent or agents into the channel and surrounding tissue. None of the prior art systems discloses a device that allows for a surgeon to perform a combination TMR and direct delivery of a therapeutic agent using a single simple device and in the same procedure.

BRIEF SUMMARY

In general, this invention is directed toward a surgical device for ablating tissue and delivering a therapeutic agent both in and near or around the ablated tissue. More specifically, this invention is directed to a system and method for creating a channel in a region of tissue and simultaneously or immediately thereafter, delivering a therapeutic agent in, near or around the channel.

The present invention comprises a device for treating tissue by creating a pathway, opening or channel in the tissue and delivering a therapeutic agent or agents into the channel with the ability to also deliver either the same or different therapeutic agents into a region of the tissue adjacent the channel. The surgical device includes an elongated multi-lumen delivery tube having a proximal end connected to a control handle assembly and extending outwardly to a treatment assembly at the distal end. An elongated tissue ablating assembly is housed and supported in a first lumen of the multi-lumen delivery tube. The ablating assembly extends through the delivery tube to an ablating tip at the treatment assembly. The ablating assembly is adapted for delivering an ablating means, such as a lasing energy from a source, such as a laser, to the ablating tip. The ablating tip is specifically designed for creating a channel, bore or other pocket into the tissue.

The multi-lumen delivery tube also houses and supports an elongated therapeutic agent delivery assembly in a second lumen. The delivery assembly has a proximal end adapted for connection with a source of the therapeutic agent or agents and extends distally through the second lumen to a delivery tip. The agent delivery assembly is adapted for transferring the therapeutic agent from the source to the delivery tip where it is dispensed into the tissue. The ablating tip and delivery tip are located adjacent each other at the distal end of the multi-lumen tube such that the therapeutic agent can be delivered into a channel formed by the ablating tip. Preferably dispensing can occur without having to remove the ablating tip from the channel.

In another embodiment of the present invention, the surgical device further includes a second elongated multi-lumen delivery tube. The second multi-lumen tube includes a plurality of lumens with the first multi-lumen tube extending through a first or main lumen. The second multi-lumen delivery tube also has at least one additional lumen that is connected with an injection receiving port at a proximal end for connection with a source of therapeutic agent or agents. The second lumen of the second delivery tube extends from the injection receiving port to a second therapeutic agent delivery tip at a distal end. The second lumen of the multi-lumen tube is adapted for delivering the therapeutic agent from the source to the second delivery tip. The first multi-lumen delivery tube extends through and is slideably within the main lumen of the second multi-lumen delivery tube. In this way, the first multi lumen tube along with the ablating and first delivery tip can be advanced into the tissue so as to ablate and create a channel and deliver a first therapeutic agent independently of the therapeutic delivery tip of the second lumen of the second multi lumen device.

The present invention further comprises a method for performing a combination myocardial revascularization procedure and delivering a therapeutic agent to a desired region of the myocardial heart tissue comprising the steps of first providing a surgical device having a first elongated multi-lumen tube with a proximal end in connection with a control handle assembly and extending to a distal treatment end. The first multi-lumen tube has a tissue ablating assembly extending through a first lumen of the multi-lumen tube and a therapeutic agent delivery assembly extending through a second lumen of the multi-lumen tube. The ablating assembly itself is connected to a source of ablating energy, such as a laser, at its proximal end and extends distally through the first lumen to an ablating tip at the end of the first multi-lumen tube. The ablating tip is adapted for creating a channel in the myocardial tissue such as a revascularization channel. The therapeutic agent delivery assembly includes a therapeutic agent injection receiving or infusion port at a proximal end and extends through the second lumen of the first multi-lumen tube to a delivery tip disposed proximally to the ablating tip such that the therapeutic agent can be delivered into the channel. And can even be accomplished without having to remove or fully retract the ablating tip from the channel.

A second elongated multi-lumen tube is aligned along the same general axis as the first multi-lumen tube. Both the first multi lumen tube and the second multi lumen delivery tube are slideably supported within and extend through a rigid or semi rigid guide tube that is connected at a proximal end to the handle assembly. The second multi-lumen tube has a proximal end in fluid connection with a second therapeutic agent and extends to an injection tip. The injection tip is adapted for delivering the second therapeutic agent into the myocardial tissue adjacent the channel.

The guide tube of the surgical device is then inserted into a patient and the treatment end, including the ablating, delivery and injection tips, is positioned adjacent the desired region of tissue. This is typically accomplished surgically with the surgeon physically locating the treatment end as desired through manipulation of the handle assembly. Once the treatment tip is located, the source of ablating energy is energized such that the ablating tip is capable of ablating the tissue. For example, a laser might be energized. The ablating tip is then advanced into the myocardial tissue to form a channel in the desired region. The injection tip is then advanced into the desired region of tissue adjacent the channel and therapeutic agent is dispensed from both the delivery tip into the channel and the injection tip into the region of tissue adjacent the channel.

In another embodiment of the procedure of the present invention, the injection tip is advanced into the myocardial tissue prior to advancing the ablating tip into the tissue to create a channel. A second therapeutic agent may be delivered from the injection tip into the tissue prior to forming the channel.

In another embodiment of the surgical device and procedure of the present invention, the surgical device further includes an elongated and at least partially flexible guide tube having a steering mechanism adapted for directing the distal end and treatment tip. The steering mechanism may be advantageously adapted such that the surgical device is useable with minimally invasive ports.

In yet another embodiment of the present invention, the surgical device and procedure are adapted for use on desired regions of tissue other than myocardial tissue.

Other objects, advantages and features of the present invention will be apparent to those of skill in the art from the following detailed description and the accompanying drawings.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 2A is a representative side view of a distal portion of the surgical device of the present invention.

FIG. 2B is a representative perspective view of the distal end of the surgical device of the present invention.

FIG. 2C is a representative side top view of an embodiment of the distal end of the surgical device of the present invention.

FIG. 3A is a representative cross sectional view of the handle and guide tube assembly of the present invention.

FIG. 3B is a representative cross sectional view of the guide tube, nosecone and actuator of the present invention.

FIG. 4A is a representative side view of the preferred embodiment of the guide tube of the present invention.

FIG. 4B is a representative cross sectional view of the preferred embodiment of the guide tube of the present invention.

FIG. 5 is a representative cross sectional view of the preferred embodiment of the multiple lumen ablating tube of the present invention.

FIG. 6A is a representative side view of the preferred embodiment of the multi-lumen therapeutic agent delivery tube of the present invention.

FIG. 6B is a representative cross sectional view of a preferred embodiment of the multi-lumen tube of the present invention.

FIG. 7 is a representative partial top view of the handle control assembly of an alternative embodiment of the surgical device of the present invention.

DETAILED DESCRIPTION

Figure 1:
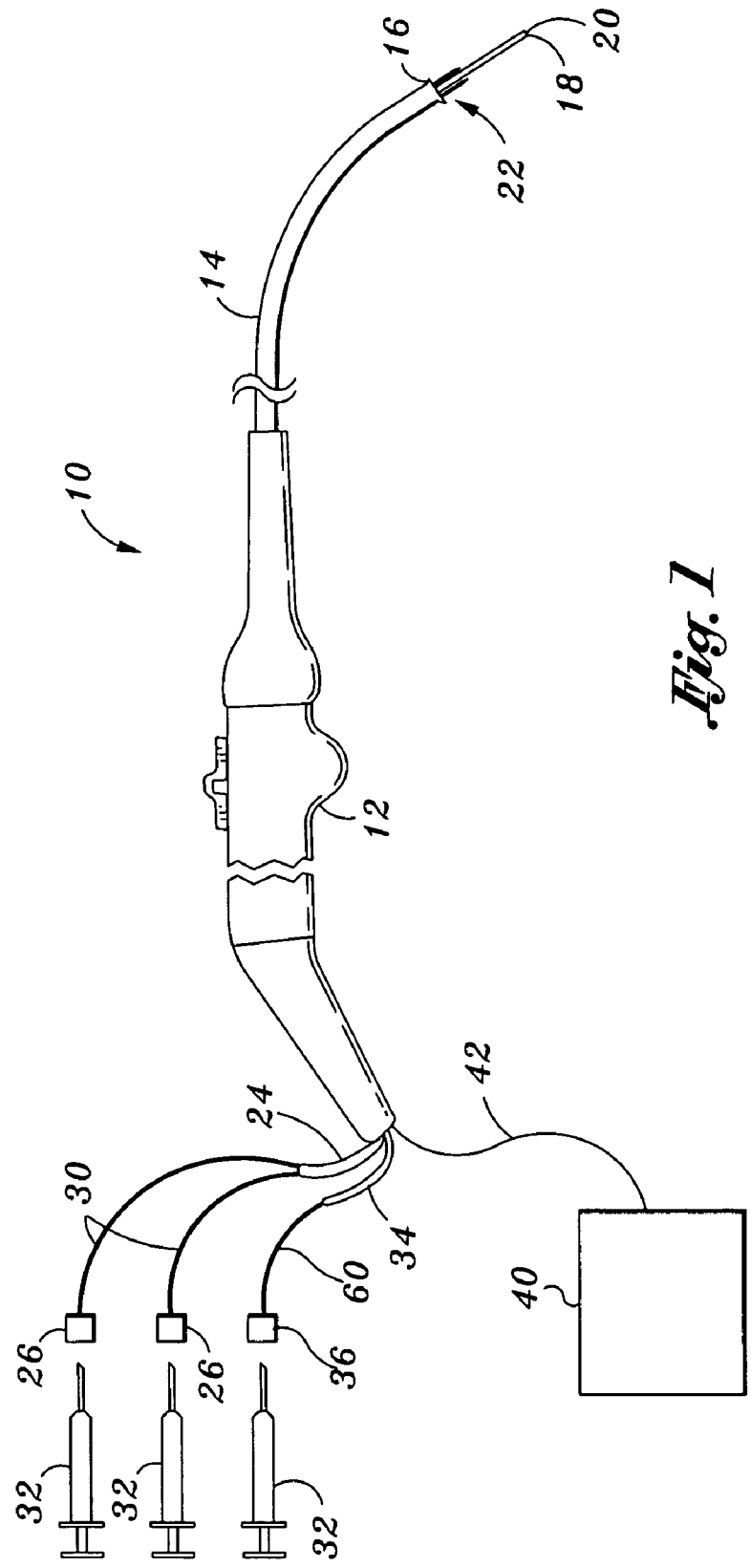
FIG. 1 is a representative schematic view of a preferred embodiment of the present invention.

While a variety of embodiments of the present invention are disclosed herein, one exemplary and the presently preferred embodiment of the surgical device is illustrated generally as reference number 10 in FIG. 1. This embodiment of the surgical device 10 is particularly suitable for procedures for treating the heart, and particularly for performing transmyocardial revascularization ("TMR"), biopsy and related procedures to a desired region of tissue in combination with the simultaneous or near simultaneous delivery of a therapeutic agent into channels formed by the TMR procedure as well as in the surrounding tissue. The illustrated dimensions are for such a TMR and therapeutic agent delivery device and procedure.

As will be discussed in greater detail, the therapeutic agent or agents may include a drug to facilitate the procedure such as a numbing agent, pain controlling substance or even a blood conditioner. Alternatively, the therapeutic agent may include a biologic agent to facilitate the procedure or recovery or even to facilitate desired results, including, but not limited to the delivery of angiogenic agents, growth factors, stem cell substances, antiarrythmic agents, chemotherapy agents, blood conditioners and even pain treating agents. The instant device and procedure further contemplate delivering multiple therapeutic agents, including delivering agents for each aspect of the procedure as well as for delivering multi-component treatments and reagents and in varying quantities, forms and dosages.

The terms "therapeutic agent," "agent," "drug" and biologic agent" shall be interchangeable for the purposes of this invention and disclosure and shall include any and all agents which could or will be used in the manners described herein, including and not limited to medications, drugs, antibiotics, vaccines, function regulators, chemotherapy agents, growth factors, stem cells, other materials for performing functions including flushing and cooling, stimulating other responses, detection, analysis, monitoring, visualization or control, etc.

The present invention further contemplates the delivery of therapeutic agents as liquid, solid, semi-solid, gel, cream, gas and also in any variety of formulation, including time release formulations, impact formulations, etc. A more detailed description of such drugs and methods of administering them is disclosed in U.S. Pat. No. 5,999,678 issued on Dec. 7, 1999 to Murphy-Chutorian, et al., which disclosure is incorporated herein in its entirety by this reference.

Referring now back to FIG. 1, the surgical device 10 is preferably adapted for hand use and manipulation and may be held in several positions using one or both hands. The device includes a handle assembly 12. A guide tube assembly 14 extends distally from the handle 12 to a distal end 16 which may include a stabilizing cup or ring 16. The stabilizing cup 16 is adapted for placement against the desired region of tissue to be treated. In the currently preferred embodiment for TMR procedure, the surgical device 10 does not include the stabilization ring 16. An ablating tip 18 and a first therapeutic agent delivery tip 20 are disposed within the open diameter of the distal end of the guide tube 16. A second therapeutic agent delivery means 22, for example a therapeutic agent injection tip assembly, is also located within the open diameter of the guide tube 14.

A first therapeutic agent delivery means 24 is adapted for delivering and dispensing a therapeutic agent or therapeutic agents from the first therapeutic agent delivery tip 20. The first therapeutic agent delivery means 24 includes a therapeutic agent receiving port 26 at a proximal end that is connected to at least one lumen of a multi-lumen delivery tube 28 (not shown). The multi lumen delivery tube 28 extends through the handle 12 and guide tube assembly 14 to a dispensing orifice on the first therapeutic agent delivery tip 20. As will be discussed further, the first therapeutic agent delivery means 24 may include one, two or more therapeutic agent receiving ports 26, such as an injection port, with each having a separate and independent conduit 30 connecting each receiving port with the first therapeutic agent delivery tip 20. The first therapeutic agent delivery tip 20 may further be adapted with multiple orifices, each connected and corresponding to an independent conduit 30 and lumen within the multi lumen delivery tube such that multiple therapeutic agents or differing application techniques may be independently administered through the first therapeutic agent delivery tip 20.

An injection device 32, such as an injection needle may be used as a source of each desired therapeutic agent and to also create sufficient pressure to deliver the agent to and out of the delivery tip 20. In the event multiple therapeutic agents are to be administered, each can be delivered from an independent injection or similar device 32.

The preferred embodiment of the surgical device also includes a second therapeutic agent delivery means 34. This second therapeutic agent delivery means 34 also includes a therapeutic agent receiving port 36, such as an injection port that is similarly connected to a conduit 60 for transferring the therapeutic agent or therapeutic agents from the receiving port to a second multi lumen delivery tube 38 (not shown). The second multi lumen delivery tube 38 passes through the handle 12 and guide tube assembly 14 and terminates at the second delivery or injection tip 22. The second therapeutic agent delivery means 34, similar to the first therapeutic agent delivery means 24, may include multiple injection ports 36, each having a separate conduit 60 for delivering the particular therapeutic agent to the second delivery tip 22 or to a unique delivery port on the second delivery tip.

A source of ablating energy 40 is connected to the ablating tip 18 through an energy transferring means 42. In the preferred embodiment, the source of ablating energy 40 is a laser and the preferred means for transferring the laser energy is through a fiber optic 42. The source of ablating energy 40 and corresponding means of transferring that energy 42, may also include, but are not limited to, radiofrequency energy, cryo-energy and cryoablation, ultrasound, mechanical means, such as rotating or vibrating energy and a shaft, as well as any other energy and means of transferring that energy or any other method of ablating tissue.

Referring now to FIGS. 2A through 2C, the preferred embodiment of the surgical device 10 is shown in greater detail. Specifically, surgical device 10 includes a handle assembly or hand piece 12 which is a molded or machined piece and preferably molded from a plastic material. The hand piece 12 defines a contoured surface and may include one or more finger grip indentations. Preferably, the contoured surface provides tactile feedback regarding the position of the hand on the device 10 and relative to the ablating tip 18 and therapeutic agent delivery tip 20 so the physician need not look away from the medical procedure or other task at hand. The contoured surface further assists the surgeon to securely hold the hand piece without slippage in at least two, different positions during either left or right handed operation of the device 10. An elongated neck portion or nosecone 44 is coupled to and extends from the hand piece 12. The nosecone 44 may be a separate component that allows for a rotary connection with the hand piece 12. As such, the nosecone 44 may include a contoured or gripping surface, include handling tabs. The nosecone 44 may also be constructed from a molded or machined plastic similar to the hand piece 12, or similarly may be constructed from other materials such as metal or composite materials.

The hand piece 12 extending into the nosecone 44 includes a continuous bore or passageway which the first multi lumen delivery tube 28 and the second multi lumen delivery tube 38 pass through. Alternatively, the housing 12 may only support a portion of each delivery tube 28 and 38. An actuator assembly 46 is coupled to the handle assembly 12. The preferred actuator 46 is a finger slide actuator used for advancing and retracting the treatment tips 18, 20 and 22. Alternatively, the handle 12 and even the nosecone 44 may be fitted with any number of actuators for such extension and retraction or other functions, including controlling the delivery of agents into the tissue. One such alternative embodiment is described in FIG. 7. In this embodiment, the first actuator 46 is used to advance and retract the ablating tip 18 while a second actuator 48 is used to advance and retract the injection or second therapeutic agent delivery tip 22. The single actuator, however, advantageously provides a simpler and less surgically complex device. Alternatively, the treatment tips 18, 20 and 22 may also be moveable using most any form of mechanical, electromechanical slide mechanism or may even be moved using an automated mechanism.

Referring now to FIGS. 2A through 3B, the actuator 46 is mechanically connected to the first multi lumen tube 28 and the second multi-lumen tube 38 such that actuation causes movement of these tubes through the guide tube 14. In the preferred embodiment, the surgical device 10 is provided with the actuator 46 in a retracted position with it being advanced forward into a fully actuated position by the surgeon during performance of the desired surgical procedure. As the actuator 46 is moved forward, it initially solely advances the first multi-lumen tube 28 which necessarily advances the ablating tip 18 and therapeutic agent delivery tip 20. This movement advantageously allows the surgeon to commence the ablation of tissue without advancing the injection tip 22. As the actuator 46 is further advanced, the second multi-lumen tube 38 is engaged and advanced along with the continuing advancement of the first multi-lumen tube 28. In this way, as the actuator 46 is advanced, first only the ablating 18 and therapeutic agent delivery tip 20 are advanced and then the injection tip 22 is also advanced. In the preferred embodiment for TMR procedures, actuation by this method is advantageous because the ablating tip 18 is required to be translated considerably further than the injection tip 22.

The guide tube 14 is a tubular sleeve that extends outwardly from its connection with the nosecone 44. Preferably, the guide tube 14 is rigidly attached to the nosecone 44 and extends into a curved distal portion 50. A stabilizing cup 16 may be attached to the distal end of the curved portion 50 for certain applications. The guide tube 14 may be constructed of metal, plastic or composite materials and may be even be malleable to allow some flexibility or made from a plastic for greater flexibility.

Referring now to FIGS. 5A and 5B in conjunction with FIGS. 2A through 3B, the preferred embodiment of the guide tube 14 is made from a thin medical grade stainless steel tube. The interior diameter of the guide tube 14 is sufficient to allow for slideable movement of the second multi-lumen tube 38 extending there through. Preferably, the inside diameter is coated or lined to reduce friction against the outer diameter of the second delivery tube 38. In the preferred embodiment, the interior of the guide tube 14 is spray coated with low friction material such as PTFE. Alternatively, the guide tube 14 may be coated or lined with any other friction reducing material, including an oil, grease, powder, polymer, etc. The friction reducing coating facilitates actuation of the actuator 46 and movement of the second multi-lumen tube 38 within the guide tube 14.

As shown, the guide tube 14 extends away from the nosecone 44 to the curved distal portion 50 which in the preferred TMR embodiment has a curve of approximately 75 degrees from its longitudinal axis. The curved portion 50 advantageously allows positioning of the treatment tips 18, 20 and 22 against the desired tissue. Depending on the procedure or even the surgeon's preferences, the guide tube 14 can be provided with a curved portion 50 of almost any angle and angle of curvature, include not having any curvature. Alternatively, the guide tube 14 may be constructed from a malleable material, semi rigid or flexible material such that the curved portion 50 may be adjustable.

Referring now to FIGS. 3A and 3B, the guide tube 14 terminates distally at the distal end 16, which may include a stabilizing cup assembly 16. The stabilizing cup 16 is generally cup or disc shaped and is designed to contact tissue and maintain contact and alignment of the treatment tips 18, 20 with the region of tissue being treated. The stabilizing cup 16 may be constructed from generally yieldable materials such as silicone, soft elastic, rubber or foam and may also be metallic or plastic. The stabilizing cup 16 includes a bore aligned and in connection with the bore formed through the guide tube 14. In this way, the treatment tips 18, 20 and 22 can freely pass through the guide tube 14 as well as the stabilizing cup 16.

Preferably, the stabilizing cup 16 is cone shaped and is made from a medical grade polyether block co-polymide polymer ("Pebax") or other medical grade polymer that is sufficiently pliable to form a contact surface with the tissue being treated and is also bondable to the distal end of the guide tube 14. Alternatively the stabilizing and locating cup 16 may be detachable with conventional snap fit or screw mount mechanisms and may be designed with differing outer diameters to accommodate different treatment procedures as well as differing access ports. The stabilizing cup 16 may also be advantageously used to allow for a suction or pressure sealing surface against the tissue with the vacuum source or pressure supply provided from a lumen of one of the multi-lumen tubes 28 or 38 or even from the guide tube 14. The stabilizing cup 16 may be omitted in applications, such as the presently described TMR application, where the downside from the increased diameter to the guide tube 14 is outweighed by the provided advantages.

FIG. 5 shows a cross sectional view of the first or inner flexible multi-lumen delivery tube 28 that is supported within and extends through the guide tube 14. Preferably, the first delivery tube 28 is made from an extruded polymer such as Pebax but could also be made from almost any medical grade material with sufficient wall strength to support multiple small diameter lumens as well as be flexible. The first multi-lumen tube 28 includes a first lumen 52 for supporting the ablating means. In the preferred TMR embodiment, the ablating means is laser energy and the first lumen 52 supports a fiber optic bundle (multifilament or monofilament) connected to a laser source 40 and adapted for delivering the laser energy from the laser through the first lumen to the ablating tip 18. The fiber optic is preferably bonded within the first lumen 52 but may also be fixed through heat or chemical shrinkage of the tube 28 or through a friction fit, wedging or the like. In this way, extending the first multi-lumen tube 28 relative to the guide tube 14 also moves the fiber optic and the ablating tip 18 as well. In the preferred embodiment, the fiber optic is bonded at the distal end of the first lumen 52 adjacent the ablating tip 18.

The first multi lumen tube 28 also includes at least one additional lumen 54 running generally alongside the first lumen 52 for delivery of one or more therapeutic agents from a source to the delivery tip 20. In the preferred TMR embodiment shown, two additional or secondary lumens 54 are provided with each terminating into the distal orifice or delivery tip 20. Multiple secondary lumens 54 also allow for delivering combinations of therapeutic agents or even epoxy-type materials that react when mixed. For example, platelet rich plasma may be mixed with a thrombin solution. When mixed, this solution will gel. Therefore, it is preferable to deliver these agents separately and allow them to mix after dispensing from the delivery tip 20.

The secondary lumens 54 deliver the therapeutic agent by directly dispensing through orifices at the distal end of the delivery tip 20. The delivery tip 20 may simply be the natural orifice at the very distal end of the secondary lumen 54 or a modified diameter orifice. Alternatively, the delivery tip 20 may be an injection needle connected to the lumen 54 or a tip specifically designed for the specific procedure or therapeutic agent being delivered.

In yet another embodiment, the distal end of one, or more if there are multiple delivery tips 20, may be capped or effectively capped with the dispensing orifice or orifices provided along the side of the delivery tip. In this configuration, the distal ends of the secondary lumens 54 are capped and an orifice or orifices are provided along the side of the lumen so as to deliver the agent out of the side of the tip. Preferably, side orifices will be placed so that any side delivery will be at least partially if not fully within the expected depth of the ablated channel. Delivery to the side may be advantageous in terms of helping to ensure that the therapeutic agent remains in the ablated channel. There also may be an advantage in creating a partial thickness channel to ensure that the agent remains within the channel created.

Capping or occluding, including partial occluding, of the distal end of the delivery tip 20 for side delivery of the therapeutic agent can be accomplished by either introducing a bond agent into the smaller secondary lumens 54 or alternatively by heating the end of the multi-lumen tubing 28. By heating to the melt temperature of the extruded tubing, the secondary lumens 54 can be melted and collapsed. Once the distal portions of the secondary lumens 54 are occluded or melted, a small hole 20 or preferably multiple small holes can be cut, drilled, machined or notched into the secondary lumens 54 proximal to the occluded distal end. A small hole can also be provided at the very distal end or tip. Preferably, the side delivery holes 20 are placed far enough proximally so that the larger profile of the multi-lumen design does not interfere with the creation of the ablated channel.

The very end of the multi-lumen delivery tube 28 can be scalloped or skived away just past the occlusions made in the secondary lumens 54 to allow the ablating tip 18 to effectively protrude distally. Alternatively, the ablating tip 18 can be bonded so it protrudes from the distal end of the multi-lumen tube 28. After the treatment tip 18 is advanced through some tissue, such as the myocardium, further advancement of the first delivery tube 28 and treatment tip 18 will allow the side holes of the delivery tip 20 and the relatively larger outer diameter of the first delivery tube 28 to be properly located within the ablated channel.

It should be understood that although the present invention discloses and contemplates a second delivery tube 38 supported within the guide tube 14, it is not a required feature for certain inventive aspects of the present invention. For example, a surgical device 10 having a single multi-lumen tube 28 with multiple therapeutic agent delivery lumens 54 and tips 20 may be advantageous in many procedures. Moreover, this design would allow for a much smaller diameter and less invasive guide tube 14 and also for an improved catheter based version for intra vascular and minimally invasive surgeries. In a single delivery tube 28 embodiment, the multi-lumen tube 28 is slideably supported within the guide tube 14 but without excess space so as to increase the overall diameter of the guide tube. To facilitate a frictionless surface, the tube 28 may be coated with a friction reducing layer such as a PTFE or even a medical grade oil or grease or silicone.

FIGS. 6A and 6B illustrate various views of the second flexible multi lumen delivery tube 38 which is adapted for carrying the first delivery tube 28 and for providing a secondary means of therapeutic agent delivery 34. Similar to the first delivery tube 28, the second delivery tube 38 is preferably made from a Pebax material or other medical grade extruded plastic. Preferably, the second delivery tube 38 is a multi-lumen tube 28 that is slideably supported within the guide tube 14 but without excess space so as to increase the overall diameter of the guide tube. To facilitate frictionless surfaces, the delivery tube 38 and/or the inner diameter of the guide tube 14 may be coated with a friction reducing layer such as a PTFE or even a medical grade oil or grease or silicone. The second delivery tube 38 is preferably proximally connected to the actuator 46 and extends through the guide tube 14 and stabilizing cup 16 to the second delivery tip 22.

The second multi-lumen delivery tube 38 includes a main or first lumen 56 which is adapted for supporting at least a portion of the first delivery tube 28. Preferably, the first delivery tube 28 is slideably supported and extends through the main lumen 56 of the second multi lumen delivery tube 28. In this way, the first delivery tube 28, including the fiber optic and ablating tip 18 can be extended or retracted independently of the second delivery tube 38 and the guide tube 14. The second delivery tube 38 also includes an additional or second lumen 58 adapted for delivering a therapeutic agent from a source to the second delivery tip 22. Preferably, the second lumen 58 is connected to the therapeutic agent receiving port 36 either directly or through a conduit 60 at the proximal end. The source of therapeutic agent may be the same therapeutic agent provided to the first delivery tube 28 or may be entirely different. For example, the second delivery tube 38 may be used to deliver a desensitizer which is injected into the tissue prior to ablating or could even be a blood coagulator that is delivered promptly after ablation. This disclosure is in no way intended to limit the various combinations of therapeutic agents that could be delivered through each of the first delivery tip 20 and the second delivery tip 22 or the various sequences of delivery of such agent.

In the preferred embodiment, the second delivery tube 38 includes three spaced apart secondary lumens 58. The main lumen 56 extends coaxially with the delivery tube 38 and the three secondary lumens 58 are equally spaced radially and circumferentially from the main lumen. Each of the secondary lumens 58 is jointly connected to a single therapeutic agent injection port 36 for delivering the therapeutic agent through a syringe or similar device. Although only a single injection port 36 is used in this embodiment for connection with multiple secondary lumens 58, any number of such ports or similar devices may be used, including using separate delivery conduits 60 and injection port 36 for each secondary lumen 58. A therapeutic agent receiving or injection port 36 or similar source of therapeutic agent could also be directly coupled to each secondary lumen 58.

Alternatively, any means of connecting a source of therapeutic agent to the secondary therapeutic agent delivery lumen 58 or to the second therapeutic agent delivery lumens 54 of the first delivery tube 28 may be used. For example a therapeutic agent infusion device could be directly coupled to any one or all of the delivery conduits 30 or 60 or even directly to the therapeutic agent delivery lumens 54 and 58. Therapeutic agent infusion devices would allow for precise dispensing of the therapeutic agent and controlled pressure of distribution. Similarly, any method of either singularly providing the therapeutic agent or individually providing the therapeutic agent to each lumen 58 may be provided as is known in the art such as through medical tubing 60.

Referring now to FIGS. 1 though 6B with particular emphasis on FIG. 2B, the distal end of the secondary lumen 58 or in the preferred embodiment, the three secondary lumens, are connected to the second therapeutic agent delivery tip 22. In the preferred embodiment, the therapeutic agent delivery tip comprises an injecting device 32 coupled to each secondary lumen 58. Similar to the therapeutic agent receiving port 36 at the proximal end, each secondary therapeutic agent delivery lumen 58 may be connected to and correspond to a unique injection device 32 or different combinations may be provided depending on the use and procedure contemplated. Alternatively, the lumens 58 may be fluidly connected as shown such that a common therapeutic agent is dispensed from the injection devices 32.

In the preferred embodiment shown, the second therapeutic agent delivery tip 22 includes three spaced apart injection needles 32. The needles 32 are spaced so as to deliver the therapeutic agent or agents directly into the tissue surrounding the ablated channel. Similar to the flexibility in the radial placement of the injection needles 32 on the second therapeutic agent delivery tip 22, each of the injection needles 32 can be varied in diameter and length to accommodate a particular procedure and desired therapeutic agent placement.

The design of the delivery tip 22, including the needles 32 for each application is particularly important so as to enable delivery of the correct amount of therapeutic agents, at the correct time and at the desired location. In the preferred TMR embodiment, it is desirable to deliver the biologic material throughout the desired region in the myocardium. For example, therapeutic agent delivery from the endocardium to the epicardium, in a controlled manner to obtain optimum coverage within the tissue and within the ablated region is desirable. For this application, typical injection needles 32 having open orifices at their distal ends or tip do not appear to provide the desired coverage within the TMR treated tissue. Thus, the distal end of each needle 32 is capped or occluded while providing the dispensing opening or ports 62 along the side length of the needle. In this way, the therapeutic agent is forced out the orifices 62 in the sides of the needles 32 instead of being delivered in a bolus at the distal tip. Early testing has shown this side dispensing to accomplish better dispersion and better delivery of the therapeutic agent into the myocardial tissue than dispensing from a traditional needle tip. Alternatively, only selected needles 32 may be end capped and provided with side delivery ports 62. Moreover, side delivery ports may be provided in combination with the traditional hollow needle or even in combination with a traditional needle having a partially occluded tip.

In the preferred needle 32 design, each of the three needles is radially spaced so they enter the tissue centered on the ablated channel. The tip of each needle 32 is capped with a point end such as a pencil point to facilitate penetrating the desired tissue. The point, however, can be in any form. The needles are of sufficient length so as to be able to pierce the heart tissue, such as epicardium or endocardium, and penetrate into the myocardium for proper delivery of the therapeutic agent to the desired ablated region of the myocardial tissue. For the preferred TMR procedure, the needles 32 are fitted with a distal hole that is approximately 1.5 mm proximal from the tip of the needle. A next hole is provided approximately 0.75 mm to 1.0 mm proximal to the first hole and 90 degrees rotated around the longitudinal axis of the needle. A third hole is provided in the needle 32 approximately 0.75 mm to 1.0 mm proximal to the second hole and 90 degrees rotated around the axis of the needle. A fourth and most proximal hole to the delivery tip 22 is provided approximately 0.75 mm to 1.0 mm proximal to the third hole and 90 degrees rotated around the axis of the needle 32. Although, the preferred embodiment has four holes, the needles 32 may include any number of holes, including one hole or a plurality of holes. The plurality of holes can be configured in any pattern. Preferentially, the holes are arrayed around the length of the needles 32.

A preferred method of the present invention involves using the surgical device 10 to perforate the desired tissue, for example, the epicardium of the heart, to create revascularization pathways or channels in combination with the delivery of at least one therapeutic agent. Although a preferred method for accomplishing a TMR procedure in combination with delivery of a biologic agent is described, the surgical device and method of the present invention is in no way limited to such procedure. For example, the method is also applicable for procedures involving other muscular or bodily tissues and even certain bone tissue. The device and method are further contemplated for procedures to treat tumors, regions of tissue affected by poor circulation and regions of tissue affected by cancer.

In a TMR procedure, myocardial tissue is ablated into pathways or revascularization channels which extends into the myocardium and may or may not communicate with the ventricle. In a typical TMR procedure, a channel approximately one millimeter in diameter is lased through the left ventricle of the heart. During lasing of the channel, the myocardium locally is disrupted which results in local healing response which is believed to help promote a local angiogenic response. The revascularization channels are created approximately one centimeter apart in the distribution of the unrevascularizable ischemic myocardium. Approximately 10 to 12 channels are created in each region of ischemic myocardium being treated.

The preferred method of the present invention for performing a combination myocardial revascularization procedure and delivering a therapeutic agent to a desired region of heart tissue requires the surgical device 10 be adapted for a TMR procedure as described in the preferred embodiment herein. The surgical device 10 is provided with the ablating tip 18, the first therapeutic agent delivery tip 20 and the injection tip 22 in the retracted position and preferably retracted within the stabilizing cup 16. By retracting the needles 32 within the stabilizing cup 16 or guide tubing 14, there is little chance for the surgeon to cause inadvertent damage, either to themselves or any of the anatomic features in the patient. This is especially important in a beating heart procedure. The surgical device 10 is also connected to the laser 40.

Once the patient is readied, a surgical opening is made and commencing with the distal end, the guide shaft 14 is inserted into the chest cavity of a patient. The surgeon then guides the device 10 and particularly the guide tube 14 to the desired region of tissue to be treated. The stabilizing cup 16 is then positioned against the desired region of the epicardium and myocardial tissue. Preferably, the surgeon adjusts the handle assembly 12 and orients the guide tube 14 such that the stabilizing cup 16 and the ablating tip 18 are positioned generally perpendicular to the surface of the tissue being treated.

Once positioned, the source of ablating energy 40 such as the laser is energized such that the ablating tip 18 is capable of ablating the tissue. The surgeon then pushes the finger slide actuator 46 forward which moves the first delivery tube 28 forward and outwardly from the guide tube 14 such that the energized ablating treatment tip 18 is extended out of the guide tube and into the tissue to create the desired channel. As the finger slide 46 is pushed further forward, the first delivery tube 28 and ablating tip 18 are moved further outwardly from the guide tube 14 ablating a deeper channel in the tissue. Further advancing of the finger slide actuator 46 engages the second delivery tube 38 so it is also moved forward and outwardly from the guide tube 14 so that the injection tip 22 and the needles 32 are forced into the tissue surrounding the channel being ablated. The creation of the channel and the engagement of the needles 32 into the surrounding tissue is a continuous operation accomplished by a single fully extended motion of the actuator 46. Alternatively, however, the actuating mechanism 44 may be adapted so as to provide the surgeon the ability to have independent control over each function of the device 10 and particularly over the movement of each delivery tube 28 and 38.

Once the channel is created and the needles 32 fully engaged into the tissue, the surgeon or assistant can administer and/or dispense the therapeutic agent or agents to the first set of therapeutic agent receiving ports 26 so that the agent or agents are delivered into the channel. Similarly, therapeutic agents can be administered and/or dispensed into the second injection port 36 or ports so they are forced out of the needles 32 into the tissue. Such dispensing and treatment can be made with accommodations as to timing of the dispensing to each location, amounts dispensed, combinations of agents, and the like.

One of the great advantages of the present surgical device 10 and the procedure of the present invention is the great flexibility to adapt the procedure and device to meet the needs of differing surgical applications. For example, the actuating mechanism may be reconfigured such that the second delivery tube 38 is advanced into the tissue for injection of a therapeutic agent prior to, and possibly again after, ablating tissue. The present invention also contemplates the use of the surgical device 10 in any combination of delivery of any combination of therapeutic agents using the first delivery tube 28 independently of the second delivery tube 38 and associated treatment tips 18, 20 & 22.

Another application of this invention is to provide a unique therapeutic agent such as a resorbable material directly into the ablated channel. Such material may include a collagen or other base material plug that is doped with another therapeutic agent or therapeutic agents. The base material may be for purposes of retention within the channel, time releasing the therapeutic agent, maintaining the channel, action of the base material, or other reason. The material could be provided directly over the fiber optic 42 in a cylindrical or partial cylindrical configuration lumen disposed in the first delivery tube 28. In this configuration, the channel is first created with the ablating tip 18 which is left in place along with the distal end of the delivery tube 28 within the channel. The resorbable material can be slid down within the main lumen 52 supporting the fiber optic 42 or alternatively through a secondary lumen 54 and out a delivery tip 20 within the channel. The fiber optic 42 could also be removed after the channel is formed in the tissue leaving a larger lumen 52 for delivery of such therapeutic agent. Similarly, the device 10 could be used to deposit an electrode, monitor or similar device into the channel while maintaining the lead within one of the lumens 28 & 38.

If a "slotted" cylinder or lumen is used (for example, a ¾ cylinder), then when the fiber is removed, the myocardium will tend to collapse the resorbable implant. The material chosen could be collagen for example or another material that is readily resorbed by the body over time. In addition, the resorbable material could be doped or impregnated with a desirable therapeutic agent or biologic material. These could be angiogenic factors to enhance the angiogenic response and also to provide a time release of the appropriate factor. As an example, stem cells or growth factors or combinations of these could be used to impregnate the resorbable implanted material.

The various therapeutic agent delivery embodiments could also be used in combination with one another. For example, a therapeutic agent delivery manifold could be supplied to provide an angiogenic compound into the myocardium surrounding the channel. The manifold may be fitted with a plurality of needles or other injection devices. In addition, a resorbable material could be provided directly within the myocardium through another lumen passing through or adjacent the manifold. In this way, the material around the channel could provide an immediate supply of the desired biologic agent to enhance the angiogenic response in the short term. A bioresorbable impregnated implanted material could also advantageously be used to provide a time dependent release of the angiogenic or other desired agent for a longer term response.

Further details of the present invention, including various methods of using the present invention may be found with reference to the Detailed Description of Embodiment section of U.S. Pat. No. 5,713,894 issued on Feb. 3, 1998 to Murphy-Chutorian and Harman and to the Detailed Description of the Preferred. Embodiment section of U.S. Pat. No. 5,976,164 issued on Nov. 2, 1999 to Bencini et al. of which both are incorporated in their entirety herein by reference.

While the principles of the invention have been made clear in illustrative embodiments and illustrations, those of skill in the art will appreciate that the present invention is capable of various other implementations and embodiments that operate in accordance with the described principles and teachings. For example, many of the components may be made from various materials and may be interconnected in various ways. Moreover, the arrangement of the elongated multi-lumen tubes and guide tube may be accomplished by using differing tubular shapes or with differing bore configurations and diameters. This is particularly contemplated as each surgical procedure may require a different treatment means and also differing surgical procedures. The handle may be made of materials other than plastic and may be configured differently to provide alternative designs. Accordingly, this detailed description is not intended to limit the scope of the present invention, which is to be understood by reference the claims below.

As also described, the preferred embodiment of the present invention is intended for use with a laser as the source of ablating energy. A Holmium or excimer laser is particularly suited to the present invention. However, any suitable laser source, pulsed or otherwise, could provide laser energy to the laser delivery means of the present invention for performing the method of the present invention. Likewise, the catheter and surgical equipment, including laser delivery means, referred to in the present document as well as that known and used in medicine and other disciplines today and in the future, will be included in the scope of this disclosure. Such laser delivery means include, but are not limited to, individual optical fibers as well as bundles of fibers, rods, mirror configurations and other laser delivery means with and without a focusing lens and the like. It will also be understood that the apparatus and method of the present invention as described herein, including novel combinations or use with any conventional mechanism or method which are known to those skilled in the art, are included within the scope of this invention.

It will further be understood that while the present invention has been generally described for performing TMR on myocardial heart tissue, the surgical device and methods described herein are equally intended for use in any suitable procedure, including but not limited to procedures where tissue ablation and therapeutic agent delivery are desired. Such treatments include but are not limited to visualization, biopsy, the treatment of tumors, cancers and other growths. The device is also suitable for stimulation procedures wherein tissue is ablated to create zones or pockets, optionally interconnected at least initially by small channels ablated through the tissue, for the introduction of blood-borne growth or other therapeutic agents or healing factors and stimulated capillary growth surrounding the lased zones or pockets to create an increased supply of oxygen to the tissue and thus a revitalization of the tissue.

What is claimed is:

1. A surgical device for ablating a channel and delivering at least one therapeutic agent into a desired region of tissue, comprising:
   (a) a first elongated multi-lumen tube;
   (b) an elongated tissue ablating assembly supported in a first lumen of the first multi-lumen tube, said ablating assembly extending from a source of laser energy into an ablating tip adapted for ablating a channel into the tissue;
   (c) a therapeutic agent delivery assembly supported in a second lumen of the multi-lumen tube, said therapeutic agent delivery assembly having a proximal end adapted for receiving a source of the therapeutic agent and extending distally through the second lumen to a delivery tip, the delivery assembly adapted for receiving the therapeutic agent and providing a conduit to the delivery tip wherein the ablating tip and therapeutic agent delivery tip are located sufficiently close such that the therapeutic agent can be delivered into a channel formed by the ablating tip; and
   (d) a second elongated multi-lumen tube having at least a first lumen and a second lumen, the first lumen supporting the first multi-lumen tube and the second lumen having a proximal end adapted for receiving a second therapeutic agent and extending through the second multi-lumen tube into a second delivery tip, said second lumen adapted for receiving the second therapeutic agent and providing a conduit to the second delivery tip;
   (e) at least one actuator operatively coupled to said first elongated multi-lumen tube and said second elongated multi-lumen tube, said at least one actuator being operatively transitional between a first retracted configuration, a second intermediate configuration and a third extended configuration, said first elongated multi-lumen tube correspondingly extending distally from said second elongated multi-lumen tube as said at least one first actuator transitions from said first retracted configuration to said second intermediate configuration, and said first elongated multi-lumen tube and said second elongated multi-lumen tube operatively extending equidistantly and along a common axis relative one another as said at least one first actuator transitions from said second intermediate configuration to said third extended configuration;
   wherein the first therapeutic agent and the second therapeutic agent are dispersed into the tissue simultaneously, in various sequences or according to a timing schedule;
   f) an outer guide tube adapted for supporting at least a portion of the first and second multi-lumen tubes; and
   g) a handle assembly for controlling the translation of the second dispensing tip relative to the ablating tip.

2. The surgical device of claim 1 wherein the first multi-lumen tube of the second elongated multi-lumen tube extends through and is slideable within the first lumen of the second multi-lumen tube.

3. The surgical device of claim 1 wherein the second delivery tip comprises an injection needle for dispensing the therapeutic agent into a region of tissue surrounding the channel.

4. The surgical device of claim 3 wherein the second delivery tip comprises a plurality of needles.

5. The surgical device of claim 3 wherein the injection needle comprises a needle having at least one dispensing port along a side for dispensing the therapeutic agent out of the side of the needle.

6. The surgical device of claim 5 wherein the injection needle further comprises a needle having a distal cap.

7. The surgical device of claim 1 wherein the first source of therapeutic agent and the second source of therapeutic agent are the same.

8. The surgical device of claim 1 wherein the first source of therapeutic agent and the second source of therapeutic agent are different.

9. The surgical device of claim 2 wherein the first multi-lumen tube and the second multi-lumen tube are flexible.

10. The surgical device of claim 1 further comprising a steering means for steering the outer guide tube and the first and second multi-lumen tubes.

11. A device for performing a combination revascularization and therapeutic agent treatment to a region of tissue, comprising:
   (a) an ablating means for receiving laser energy and delivering it to an ablating tip, the ablating means having a proximal end adapted for connection with a source of the laser energy and extending to the ablating tip for creating a channel in the tissue;
(b) a first therapeutic agent delivery assembly having a proximal end adapted for connection to a first source of therapeutic agent and extending distally to a delivery tip, said delivery tip disposed proximally to the ablating tip such that the therapeutic agent may be dispensed directly into the channel;
(c) a second therapeutic agent delivery assembly having a proximal end adapted for connection to a second source of therapeutic agent and extending distally to an injection tip for injecting the therapeutic agent directly into tissue adjacent the channel; and
(d) a guide tube supporting the ablating means, the first therapeutic agent delivery assembly and the second therapeutic agent delivery assembly;
(e) a first actuator operatively coupled to said ablating means and said first therapeutic agent delivery assembly and operative to linearly extend said delivery tip and said ablating tip into said region of tissue and selectively retract said delivery tip and ablating tip therefrom;
(f) a second actuator operatively coupled to said second therapeutic agent delivery assembly and operative to selectively extend and retract said injection tip from said region of tissue,
wherein the first therapeutic agent delivery assembly and the second therapeutic agent delivery assembly are capable of delivering at least a first therapeutic agent and a second therapeutic agent into the region of tissue simultaneously, in various sequences or according to a timing schedule, said first actuator and said second actuator operating independently of one another; and
g) a handle assembly in connection with the second therapeutic aunt delivery assembly and the guide tube, the handle having a control mechanism for controlling the extension of the injection tip relative to the guide tube.

12. The device of claim 11 wherein the handle assembly further comprises a second control mechanism and wherein actuation the second control mechanism translates injection tip to extend outwardly from the distal end of the guide tube.

13. The device of claim 11 wherein the guide tube assembly curves towards its distal end.

14. The device of claim 11 further comprising a steering assembly for steering the guide tube assembly.

15. The device of claim 11 wherein the guide tube assembly comprises a rigid tube.

16. The device of claim 11 wherein the guide tube assembly comprises a flexible tube.

17. The device of claim 12 wherein the guide tube includes a curve of approximately 70 degrees from an elongated lateral axis.

18. The device of claim 12 wherein the guide tube includes a curve of between 60 degrees and 90 degrees from an elongated lateral axis.

19. The device of claim 12 wherein the curve is between approximately 0 degrees and 130 degrees from an elongated lateral axis.

20. The device of claim 11 wherein the distal end of the guide tube comprises a locating cup for locating the lasing tip and biologic treatment tip on the desired region of tissue.

21. A transmyocardial revascularization and therapeutic agent delivery system comprising:
a) a first elongated multi-lumen tube;
b) a first therapeutic agent delivery assembly having a proximal end adapted for connection with a source of a first therapeutic agent and extending through a lumen of the first multi-lumen tube to a first therapeutic agent delivery tip;
c) a second elongated multi lumen tube extending through a second lumen of the first multi lumen tube;
d) a revascularization treatment assembly having a proximal end adapted for connection with an ablating energy and extending through a first lumen of the second multi-lumen tube to an ablating tip;
e) a second therapeutic agent delivery assembly having a proximal end adapted for connection with a source of therapeutic agent and extending through a second lumen of the second multi-lumen lumen tube to a second therapeutic agent delivery tip; and
f) a control mechanism in connection with the first multi-lumen tube and the second multi-lumen tube and adapted such that actuation of the control assembly extends the ablating tip and second therapeutic agent delivery tip relative the first therapeutic agent delivery tip and thereafter operatively extends the ablating tip, second therapeutic agent delivery tip and said first therapeutic agent delivery tip distally about a common axis;
wherein the first therapeutic agent delivery assembly and the second therapeutic agent delivery assembly are capable of delivering at least a first and a second therapeutic agent into the region of tissue simultaneously, in various sequences or according to a timing schedule;
g) a handle assembly supporting the control mechanism;
h) a guide tube extending from the handle assembly to a distal end, said first multi-lumen tube extending through and slideably supported within said guide tube; and
i) a laser in connection with a fiber optic that extends through the second multi-lumen lumen tube to the ablating tip.

22. The transmyocardial revascularization system of claim 21 wherein the first therapeutic agent delivery tip comprises a hollow dispensing needle.

23. The transmyocardial revascularization system of claim 22 wherein the dispensing needle comprises at least one port on a side of the needle for dispensing the therapeutic agent laterally into the treatment area.

24. The transmyocardial revascularization system of claim 23 wherein the dispensing needle is end capped.

25. The transmyocardial revascularization system of claim 21 wherein the second multi-lumen tube is slideably supported within the second lumen of the first multi-lumen tube.

26. The transmyocardial revascularization system of claim 21 wherein the second multi-lumen tube comprises the revascularization assembly and at least one lumen for delivering the therapeutic agent.

* * * * *